(12) United States Patent  
Cogger

(10) Patent No.: US 6,506,183 B2  
(45) Date of Patent: Jan. 14, 2003

(54) ONE SHOT ACTUATION HOUSING APPARATUS FOR INSTILLING A MEDICATION INTO AN EYE

(75) Inventor: John J. Cogger, Irvine, CA (US)

(73) Assignee: Advanced Medical Optics, Santa Ana, CA (US)

( * ) Notice: Subject to any disclaimer, the term of this patent is extended or adjusted under 35 U.S.C. 154(b) by 203 days.

(21) Appl. No.: 09/776,826

(22) Filed: Feb. 2, 2001

(65) Prior Publication Data

US 2002/0107493 A1 Aug. 8, 2002

(51) Int. Cl.$^7$ ............................................. A61M 35/00
(52) U.S. Cl. ...................... 604/298; 604/218; 604/311; 604/294; 604/295
(58) Field of Search .................. 604/298, 218, 604/311, 294, 295, 231, 246, 289, 19, 46, 48, 68

(56) References Cited

U.S. PATENT DOCUMENTS

| | | | |
|---|---|---|---|
| 4,792,334 A | 12/1988 | Py | 604/301 |
| 4,908,024 A | 3/1990 | Py et al. | 604/300 |
| 4,946,452 A | 8/1990 | Py | 604/301 |
| 4,981,479 A | 1/1991 | Py | 604/302 |
| 5,085,651 A | 2/1992 | Py | 604/298 |
| 5,133,702 A | 7/1992 | Py | 604/302 |
| 5,163,929 A | 11/1992 | Py | 604/298 |
| 5,267,986 A | 12/1993 | Py | 604/294 |
| 5,320,845 A | 6/1994 | Py | 424/427 |
| 5,401,259 A | 3/1995 | Py | 604/294 |
| 5,499,751 A | 3/1996 | Meyer | 222/386 |
| D368,774 S | 4/1996 | Py | D24/113 |
| D374,719 S | 10/1996 | Py | D24/120 |
| 5,613,957 A | 3/1997 | Py | 604/294 |
| 5,641,004 A | 6/1997 | Py | 141/3 |
| 5,685,869 A | 11/1997 | Py | 604/294 |
| 5,746,728 A | 5/1998 | Py | 604/298 |
| 5,855,322 A | 1/1999 | Py | 239/11 |

*Primary Examiner*—Manuel Mendez
*Assistant Examiner*—Kathryn L. Thompson
(74) *Attorney, Agent, or Firm*—Walter A. Hackler; Peter Jon Gluck

(57) ABSTRACT

Apparatus for operating eye drop dispenser is provided which includes a four bar link system in order to enable cocking firing and resetting of an actuator for dispensing eye drops upon a single button depression by a patient.

22 Claims, 3 Drawing Sheets

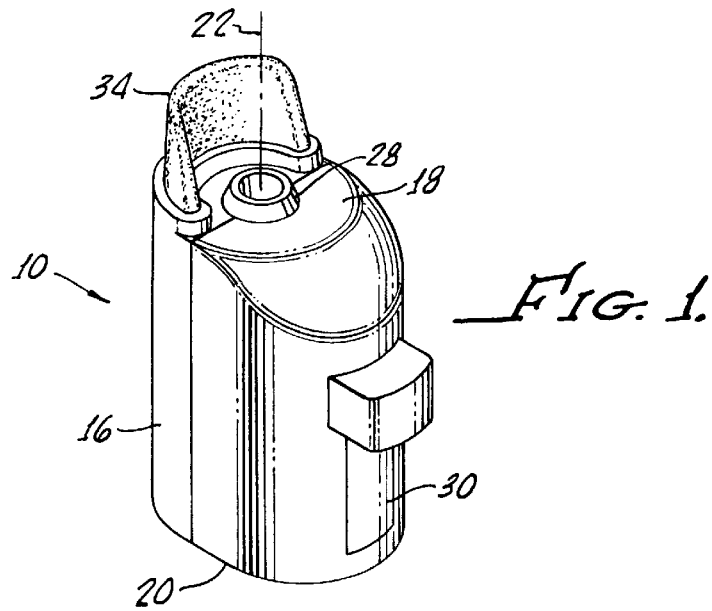
FIG. 1.
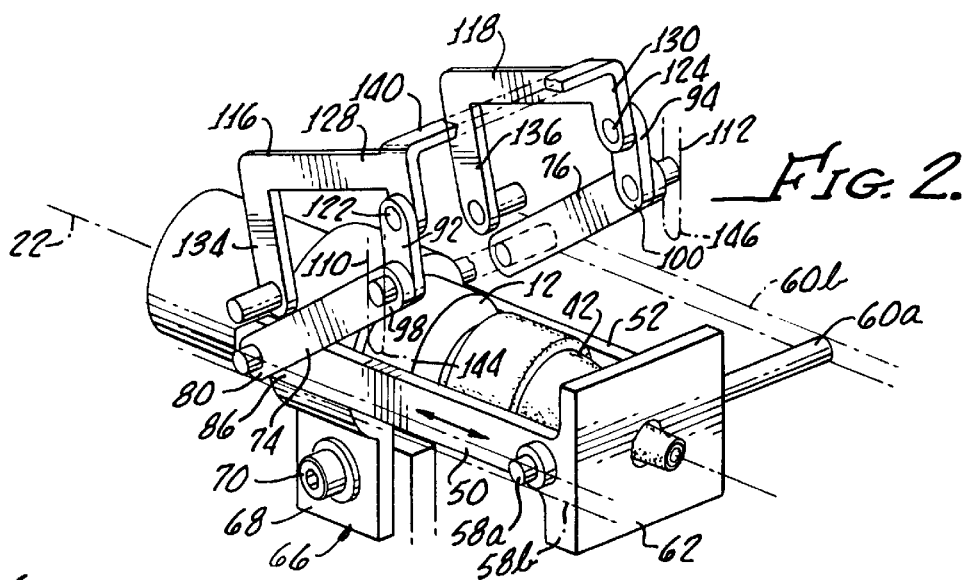
FIG. 2.
FIG. 3.

ONE SHOT ACTUATION HOUSING APPARATUS FOR INSTILLING A MEDICATION INTO AN EYE

The present invention generally relates to apparatus for dispensing microliter amounts of medicament and is more particularly directed to apparatus for instilling a medicament into an eye.

A great number of devices have been developed for instilling medicament to an eye. Well known eye drop containers conventionally include a squeezable container and a nozzle for releasing drops of medicament into the eye by compression of the container. Obviously, this apparatus affords no practical method of dispensing a measured, or metered, dose of medicament inasmuch as the liquid dispensed from the nozzle is dependent upon the amount of compression of the container. Thus, there is no way of accurately controlling the volume of each dose of medicament released into the eye and, further, the smallest drop obtainable is the result of the combined effective gravity and surface tension.

When preservative-free medicaments are utilized, simple eye drop dispensers are not practical because there are no means for preventing the tip from being contaminated due to its exposure to air. Such tip contamination ultimately spreads to the medicament in the container.

In an attempt to overcome these problems, apparatus has been developed for applying a medicament to an eye which includes a nozzle having a seam which is normally in a closed position for preventing the passage of medicament through the nozzle, and which opens in response to a flow of medicament of sufficient pressure to enable opening of the seam in order to permit the passage of medicament through the nozzle for release into the eye, see U.S. Pat. No. 5,685,869.

While this nozzle is suitable, there is difficulty in coupling the nozzle with a suitable reservoir of medicament in order to create a working, producible device for multiple dose delivery of a preservative-free product of sufficient dose accuracy for consumer benefit and regulatory body registration over an extended period of time of up to six months or more.

Operation of prior art devices such as set for the in the hereinabove referenced U.S. Patent typically cause a small negative pressure or vacuum within the medicament container during operation. When a collapsible container is utilized to accommodate shrinking of volume of the medicament reservoir, the materials of construction do not satisfactorily inhibit the permeating of air through the container walls to provide a desired long term use in storage of the device without compromise of the stored medicament.

U.S. patent application Ser. No. 09/435,703 filed Nov. 8, 1999 entitled MULTIPLE PRECISION DOSE PRESERVATIVE FREE MEDICATION DELIVERY SYSTEM provides a nozzle and medicament reservoir combination that enables multiple dose delivery of a preservative-free product with accurate dose dispensing over extended periods of time.

As described in this reference a spring in an actuator is compressed by a button disposed at a rear of a housing. This compression causes a fluid reservoir the actuator together. The compressed condition is held by a latching mechanism and upon release of the latch, by a trigger, the two parts are rapidly accelerated apart from each other in an axial direction and the actuator or pump, produces a dose that is sprayed out of a nozzle.

SUMMARY OF THE INVENTION

The present invention includes apparatus for instilling a medicament into an eye, an apparatus for operating an eye drop dispenser.

The apparatus generally includes a housing having a front and a rear with a longitudinal axis therebetween with a reservoir disposed in the housing for containing a medicament. A nozzle is provided and disposed approximate the housing front for instilling a dose of the medicament into an eye and a spring driven actuator is provided for metering doses of medicament from the reservoir to the nozzle and forcing each metered dose through the nozzle upon forward axial displacement of the actuator by the spring along the longitudinal axis.

More particularly, the apparatus includes a drawbar disposed for longitudinal movement within the housing and along the reservoir. The drawbar includes a front end for engaging the actuator in order to compress the spring upon rearward longitudinal movement of the drawbar and a connecting rod having a first end, pivotally attached of a second end of the drawing bar, is provided for causing rearward longitudinal movement of the drawbar upon pivoting of the connecting rod toward the drawbar. In this operation, the spring is compressed.

A push link is provided which includes a first end, pivotally attached to a second end of a connecting rod, for pivoting the connecting rod toward the draw bar and a track guides the push link toward the drawbar.

An actuator lever, pivotally attached to a second end of the push link, enables manual urging of the push link along the track.

Importantly, the push link has sufficient length for enabling the lever to urge the push link first end past an end of the track to cause release of the compressed spring, concomitant longitudinal movement of the drawbar and actuation of the actuator without release of the lever.

Thus, the apparatus may be operated by a simple depression of the actuator lever without having to release the lever or to separately activate the activator by either a spaced apart trigger or a second depression of the lever. Hence, a single depression of the actuator lever provides for "one shot" actuation for metering a single dose of medicament into an eye.

More particularly, the track may be disposed in a generally perpendicular relationship to the drawbar and the lever may have a first end pivotally attached to the push link second end and the second end pivotally attached to the housing. To accommodate for this relationship, the lever may have an L shape.

In a disposable embodiment of the present invention a clamp is provided for fixing the dispenser reservoir within the housing. In another embodiment of the present invention, a sleeve is provided for holding the dispenser and the reservoir within the housing. In this embodiment, the sleeve receives the dispenser in a replaceable manner and the drawbar first end is pivotally attached to the drawbar for enabling replacement of the dispenser in the sleeve.

Preferably, the present invention includes a pair of drawbars, a pair of connecting rods, a pair of push links, a pair of tracks and a pair of actuation lever disposed on opposite sides of the dispenser. In this instance, an actuator bar interconnects the lever first ends and is disposed on a side of a housing for enabling simultaneous depression of the actuation levers.

BRIEF DESCRIPTION OF THE DRAWINGS

The advantages and features of the present invention will be better understood by the following description when considered in conjunction with the accompanying drawings in which:

FIG. 1 is a perspective view of the apparatus in accordance with the present invention generally showing a housing, a nozzle, and an actuator lever;

FIG. 2 is a perspective view of apparatus in accordance with the present invention without a housing and exploded to show an interrelationship between a drawbar, connecting rod, push link and actuator lever;

FIG. 3 is a cross-sectional view of the present invention generally showing the housing, actuation lever, draw bar, connecting rod, and a clamp for securing a dispenser within the housing;

DETAILED DESCRIPTION

Figure 4:
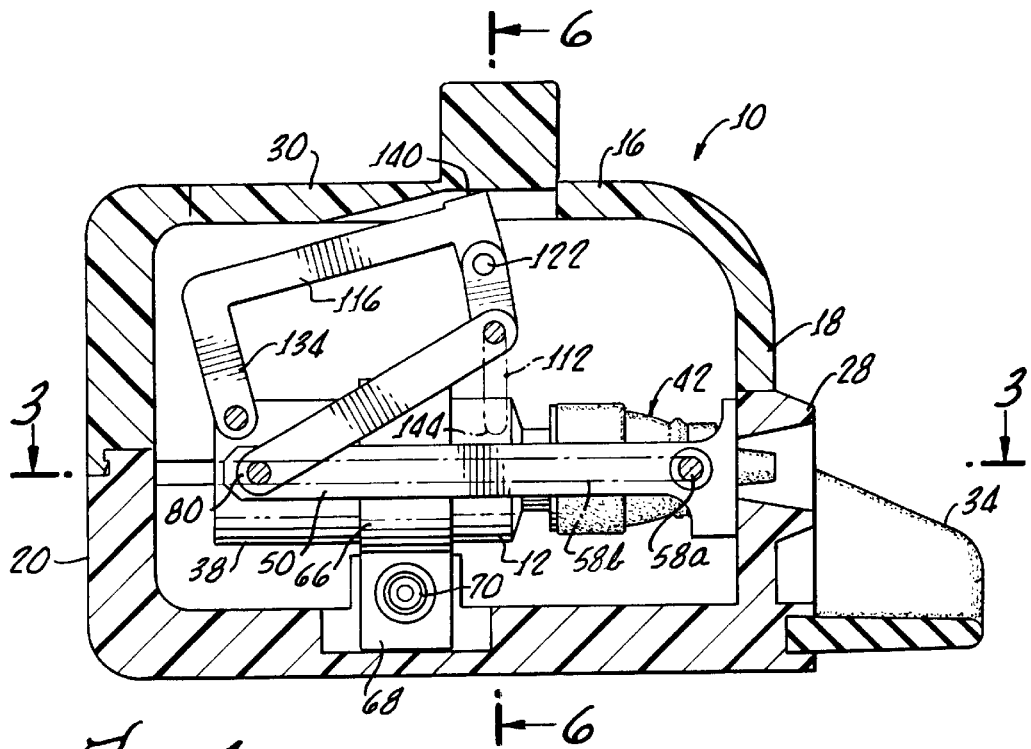
FIG. 4 is a partial side cross-section of the apparatus in accordance with the present invention showing linkage coordination between the draw bar, connecting rod, push link and actuation lever before one-shot dispensing of a metered dose of medicament.

With reference to FIG. 1, there is shown apparatus 10 for instilling a medicament into an eye and also for operating an eye drop dispenser 12, see FIG. 2, for instilling a medicament into an eye (not shown). The apparatus 10 generally includes a housing 16 having a front 18 and a rear 20 with a longitudinal axis 22 therebetween.

With continued reference to FIG. 1, a nozzle 28 disposed proximate the housing front 18 is provided for instilling a dose of medicament (not shown) into an eye (not shown) upon compression of an actuator lever 30 as will be hereinafter discussed in greater detail.

Components of the apparatus 10 may be formed from conventional materials suitable for use with devices for dispensing medication in eyes.

A support member 34 may be fixed to the housing 16 in order to steady the nozzle 28 at a fixed distance from a patient's eye (not shown) as is well known in the art.

With reference to FIG. 3, the dispenser 12 includes a reservoir 38 and a spring 40 driven actuator 42 for metering doses of medicament from the reservoir 38 to the nozzle 28 and forcing each metered dose through the nozzle 28 upon forward displacement as shown by the arrow 46 of the actuator 42 by the spring 40 along the longitudinal axis 22.

The nozzle 28, reservoir 38, spring 40 and actuator 42 are fully described both in structure and function in U.S. patent application Ser. No. 09/435,703 entitled "Multiple Precision Dose, Preservative Free Medication Delivery System" filed Nov. 8, 1999, as well as in U.S. patent application Ser. No. 09/707,006 entitled "Twist Housing Apparatus For Instilling A Medication Into An Eye" filed Nov. 6, 2000, and U.S. patent application Ser. No. 09/685,523 entitled "Housing Apparatus With Rear Activated Button For Instilling A Medication Into An Eye" filed Oct. 10, 2000. These applications are incorporated herewith in their entirety, including all specifications and drawings, by this specific reference thereto for the purpose for describing the dispenser 12 including a nozzle 28, reservoir 24, spring 40 and actuator 42 as well as the operation thereof.

Figure 5:
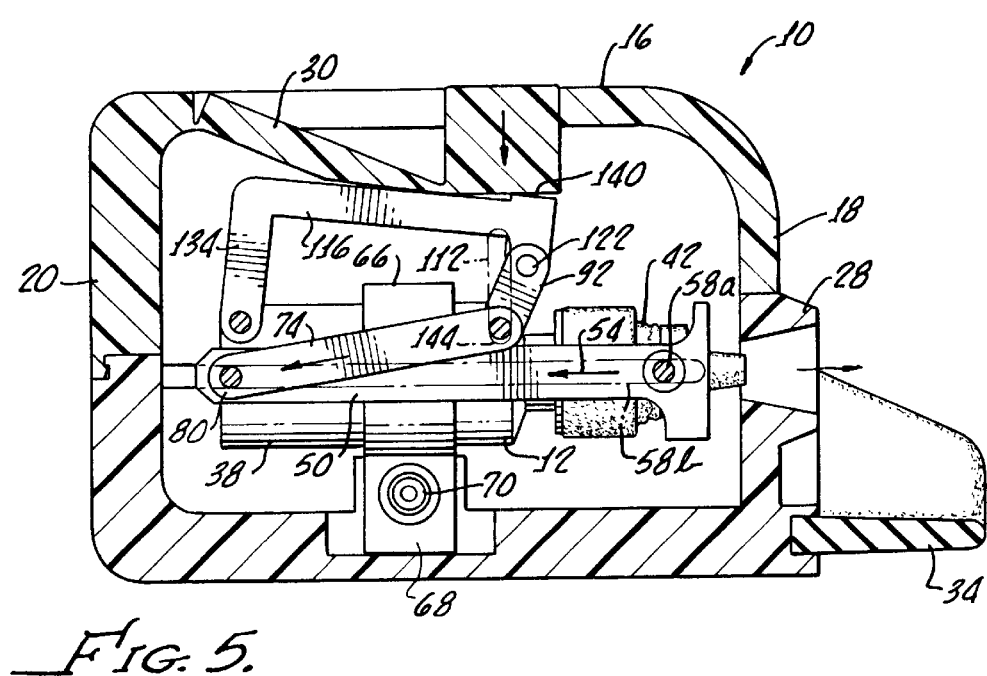
FIG. 5 is a view of apparatus in accordance with the present invention similar to FIG. 4 as showing depression of the actuation lever in order to provide for one-shot dispensing of a metered dose of medicament.

With further reference to FIGS. 4 and 5, the apparatus 10 includes drawbars 50, 52 disposed for longitudinal movement, as shown by the arrow 54 in FIG. 5, within the housing 16 and along the reservoir 38. The drawbars 50, 52 each include first ends 58, 60 with a face plate 62 therebetween for engaging the actuator 42 in order to compress the spring 40 upon rearward movement of the draw bars 50, 52 as indicated by the arrow 54, the compressed spring 40 not being shown in the Figures but its operation and compressed state being shown in the hereinabove referenced and incorporated patent application. Rods 58a, 60a engage slots 58b, 60b in order to guide the drawbars 50, 52.

Figure 6:
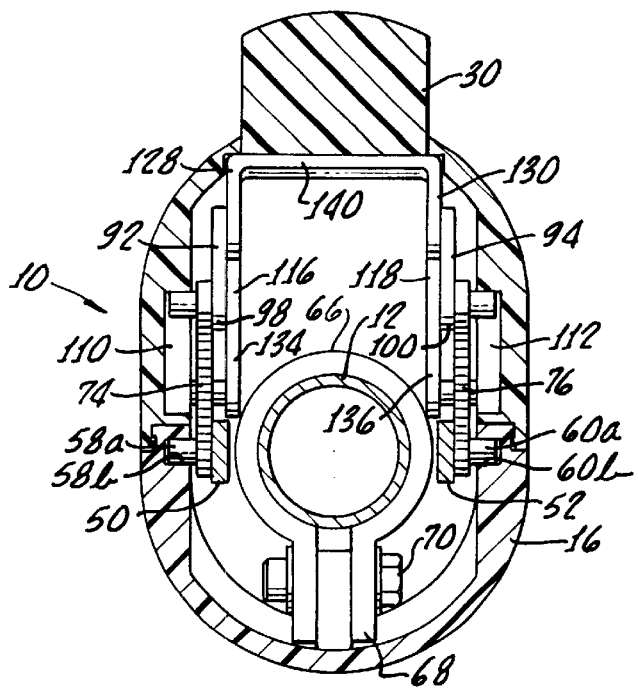
FIG. 6 is a cross-sectional plan view of the apparatus shown in FIGS. 2 and 3.

The reservoir 38 may be fixed within the housing 16 by way of the clamp 66, see FIG. 2 and FIG. 6 which may be tightened around the reservoir with a flange 68 through which a bolt 70 passes. Connecting rods 74, 76 are provided and have first ends 80, 82 pivotally attached to second ends 86, 88 of the draw bars 50, 52 for causing rearward longitudinal movement of the drawbars 50, 52 as indicated by the arrow 54 in FIG. 5 upon pivoting of the connecting rods 74, 76 toward the drawbars 50, 52.

Push links 92, 94 having first ends 98, 100 pivotally attached to second ends 104, 106 of connecting rods 74, 76 are provided for pivoting the connecting rods 74, 76 toward the draw bars 50, 52.

Tracks 110, 112, which may be formed in the housing 16 are provided for guiding the push links 92, 94 toward the draw bars 50, 52 as most clearly shown in FIGS. 4 and 5, FIG. 4 showing a rest position in which the actuator lever 30 protrudes from the housing 16 before depression thereof to activate the actuator 42 and FIG. 5 showing the actuator lever depressed for moving the actuator 42 rearward. FIG. 5 shows the alignment of the draw bars 50, 52, connecting rod 74, 76 and push links 94, 96 just before release of the spring 40 from a compressed state, the release being hereinafter described.

Actuator levers 116, 188, which may be L-shaped are pivotally attached to second ends 122, 124 for enabling manual purging of the push links 92, 94 along the tracks 110, 112.

The tracks 110, 112 are disposed generally perpendicular to the drawbars 50, 52. The actuation levers 116, 118 include ends 128, 130 pivotally attached to the push link second ends 122, 124 and second ends 134, 136 pivotally attached to the housing 116. A bridge 140 interconnecting the actuation lever first ends 128, 130 facilitates simultaneous movement of the actuation 116, 118 by depression of the actuator button 30.

Importantly, the push links 92, 94 have a length sufficient for enabling the levers 116, 118 to push the push link first ends 98, 100 past track ends 144, 146 to cause release of the compressed spring 40, forward longitudinal movement of the draw bars 50, 52 and actuation of the actuator without release of the actuator button 30 or actuation levers 116, 118.

When the push link first ends 98, 100 pass the track ends for 144, 146 the push links 94, 96 pivot about second ends 122, 124 freeing the draw bars,150, 152 which then move forwardly in a direction opposite the arrow 54 shown in FIG. 5. Thus, the spring 40 not only actuates the actuator 42 but also resets the drawbars 50, 52 in forward positions as shown in FIG. 4.

Forward movement of the drawbars 50, 52 is independent of the position of the button 30. That is, the button may be held in the position in FIG. 5 while the drawbars 50, 52 move forward upon actuation of the actuator 42. Subsequent release of the button 30 enables the push link first ends 92, 94 to then reengage the tracts 110, 112.

The present invention provides for the automatic reversing of the drawbars 50, 52 after the actuator 42 is cocked. At the last downward portion of the push links 92, 94 stroke, the drawbars 52, 54 are released and the spring 40 acts to push the drawbars 50, 52 back to their initial positions. It is not necessary for a patient to release the button 30 for the drawbars 50, 52 to return to their rest positions as shown in FIG. 4. The internal process of cocking, firing and reset are not obvious to the patient and when the button 30 is finally released by the patient, another shot may be immediately be fired as the apparatus 10 is automatically reset.

Figure 7:
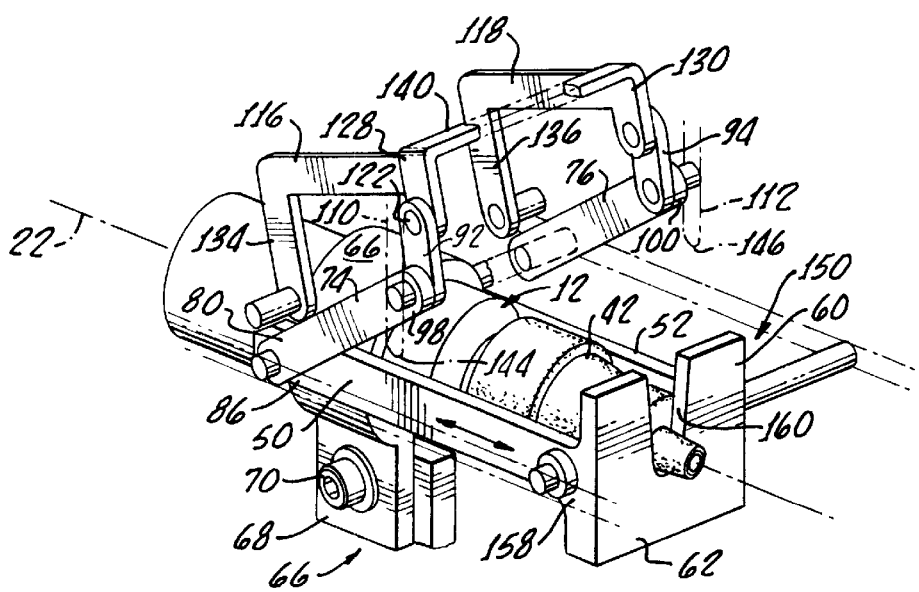
FIG. 7 is an alternative embodiment of the present invention in which a sleeve is provided for holding a dispenser within the housing (not shown) and a face plate interconnecting a pair of draw bars and pivotally thereon for enabling of replacement of the dispenser in the sleeve.

With reference to FIG. 7 there is shown an alternative embodiment of the present invention with common character references referring to identical or substantially similar components as hereinabove discussed in connection with the embodiment 10 shown in FIGS. 1–6.

The apparatus 150 includes a sleeve 154 for removably receiving the dispenser 12. In addition, a faceplate 62 is attached to draw bar first ends 58, 60 by pivots 158 for enabling placement of the dispenser 12 in the sleeve 154. The removable dispenser may be facilitated by a slot 160 in the faceplate 62 and the pivot 158 may include a snap or resistance mechanism for holding the face plate 62 generally perpendicular to the draw bars 50, 52 during operation of the apparatus 150.

Although there has been hereinabove described apparatus for dispensing eye drops in accordance with the present invention for the purpose in illustrating the manner in which the invention may be used to advantage, it will be appreciated that the invention is not limited thereto. Accordingly, any and all modifications, variations, or equivalent arrangements which may occur to those skilled in the art should be considered to be within the scope of the invention as defined in the appended claims.

What is claimed is:

1. Apparatus for operating an eye drop dispenser, said eye drop dispenser including a reservoir for containing a medicament, a nozzle for instilling a dose of the medicament into an eye and a spring driven actuator for metering doses of medicament from said reservoir to said nozzle and forcing each metered dose through said nozzle upon axial displacement of the actuator by the spring driven actuator along a longitudinal axis, said apparatus comprising:

a housing for supporting the dispenser, the reservoir being fixed within a sleeve;

a drawbar disposed for longitudinal movement within said housing and along said reservoir, said drawbar having a first end for engaging the actuator in order to compress the spring upon rearward longitudinal movement of said drawbar;

a connecting rod, having a first end pivotally attached to a second end of said drawbar, for causing the rearward longitudinal movement of said drawbar upon pivoting of said connecting rod toward said drawbar;

a track for guiding a push link toward said drawbar; and an actuator lever, pivotally attached to a second end of said push link along said track, said push link having sufficient length for enabling the lever to urge a push link first end past an end of said track to cause release of the compressed spring, forward longitudinal movement of said drawbar and actuation of the actuator without release of the lever.

2. The apparatus according to claim 1 wherein said track is disposed generally perpendicular to said drawbar.

3. The apparatus according to claim 2 wherein the lever has a first end pivotally attached to the push link second end and a second end pivotally attached to said housing.

4. The apparatus according to claim 3 wherein the lever has an L shape.

5. The apparatus according to claim 4 further comprising a clamp for fixing the dispenser reservoir within said housing.

6. The apparatus according to claim 4 further comprising a sleeve for replaceably receiving the dispenser reservoir.

7. The apparatus according to claim 6 wherein the drawbar first end is pivotally attached to said drawbar for enabling replacement of the dispenser in said sleeve.

8. Apparatus for operating an eye drop dispenser, said eye drop dispenser including a reservoir for containing a medicament, a nozzle for instilling a dose of the medicament into an eye and a spring drawn actuator for metering doses of medicament from the reservoir to said nozzle and forcing each metered dose through said nozzle upon forward axial displacement of the actuator by the spring driven actuator along a longitudinal axis, said apparatus comprising:

a housing for supporting the dispenser, the reservoir being fixed within said housing;

a pair of drawbars disposed for longitudinal movement within said housing along said reservoir, said reservoir being disposed between the drawbars, each drawbar having a first end for engaging the actuator in order to compress the spring upon rearward longitudinal movement of the drawbars;

a pair of connecting rods each having a first end pivotally attached to a corresponding second end of the drawbars, for causing the rearward longitudinal movement of the drawbars upon pivoting of the connecting rods toward respective drawbars;

a pair of push links, each having a first end pivotally attached to a corresponding second end of the connecting rods, for pivoting the connection rods toward the drawbars;

a pair of tracks, each track being disposed for guiding a corresponding push link toward a corresponding connecting rod;

a pair of actuation levers each pivotally attached to a corresponding second end of the push links, for enabling manually engaging of the push links along the tracks, the push links having sufficient length for enabling the lever to engage the first ends of the push links past ends of each track to cause release of the compressed spring, forward longitudinal movement of the drawbars and acceleration of the actuator without release of the levers.

9. The apparatus according to claim 8 wherein the tracks are disposed generally perpendicular to the drawbars.

10. The apparatus according to claim 9 wherein each lever has a first end pivotally attached to a corresponding push link second end and a second end pivotally attached to said housing.

11. The apparatus according to claim 10 further comprising a bridge interconnecting the lever first ends.

12. The apparatus according to claim 1 whereas each lever has an L shape.

13. The apparatus according to claim 12 further compresses a clamp for fixing the dispenser reservoir within said housing.

14. The apparatus according to claim 12 further comprising a sleeve for replaceably receiving the dispenser reservoir.

15. The apparatus according to claim 14 further comprising a face plate pivotally attached between the drawbar first ends for enabling replacement of the dispenser in said sleeve.

16. Apparatus for instilling a medicament into an eye, said apparatus comprising:
- a housing having a front and a rear with a longitudinal axis therebetween;
- a reservoir disposed in said housing for containing a medicament;
- a nozzle disposed proximate the housing front for instilling a dose of the medicament into an eye;
- a spring driver actuator for metering doses of medicament from said reservoir to said nozzle and forcing each metered dose through said nozzle upon forward axial displacement of the actuator by the spring driven actuator along the longitudinal axis;
- a drawbar disposed for longitudinal movement within said housing and along said reservoir, said drawbar having a first end for engaging the actuator in order to compress the spring upon rearward longitudinal movement of said drawbar;
- a connecting rod, having a first end pivotally attached to a second end of said drawbar, for causing the rearward longitudinal movement of said drawbar upon pivoting of said connecting rod toward said drawbar;
- a push link, having a first end pivotally attached to a second end of said connecting rod for pivoting said connecting rod toward said drawbar;
- a track for guiding said push link toward said drawbar; and
- an actuator lever, pivotally attached to a second end of said push link for enabling manual urging of said push link along said track, said push link having sufficient length for enabling the lever to urge the push link first end past an end of said rack to cause release of the compressed spring, forward longitudinal movement of said drawbar and acceleration of the actuator without release of the lever.

17. The apparatus according to claim 16 wherein said track is disposed generally perpendicular to said drawbar.

18. The apparatus according to claim 17 wherein the lever has a first end pivotally attached to the push link second end and a second end pivotally attached to said housing.

19. The apparatus according to claim 18 wherein the lever has an L shape.

20. The apparatus according to claim 19 further comprising a clamp for fixing the dispenser reservoir within said housing.

21. The apparatus according to claim 19 further comprising a sleeve for replaceably receiving the dispenser reservoir.

22. The apparatus according to claim 21 wherein the drawbar first end is pivotally attached to said drawbar for enabling replacement of the dispenser in said sleeve.

* * * * *